United States Patent
Imanishi et al.

(10) Patent No.: US 7,053,199 B2
(45) Date of Patent: May 30, 2006

(54) NUCLEOSIDE ANALOGS AND OLIGONUCLEOTIDE DERIVATIVES CONTAINING THESE ANALOGS

(75) Inventors: Takeshi Imanishi, 2-18, Chiyogaoka 2-chome, Nara-shi, Nara 631-0045 (JP); Satoshi Obika, Osaka (JP)

(73) Assignee: Takeshi Imanishi, Nara (JP)

( * ) Notice: Subject to any disclaimer, the term of this patent is extended or adjusted under 35 U.S.C. 154(b) by 310 days.

(21) Appl. No.: 10/363,057

(22) PCT Filed: Aug. 29, 2001

(86) PCT No.: PCT/JP01/07400

§ 371 (c)(1),
(2), (4) Date: Feb. 28, 2003

(87) PCT Pub. No.: WO02/18388

PCT Pub. Date: Mar. 7, 2002

(65) Prior Publication Data

US 2004/0192918 A1 Sep. 30, 2004

(30) Foreign Application Priority Data

Aug. 29, 2000  (JP) .................................... 2000-259290

(51) Int. Cl.
*C07H 21/00* (2006.01)
*C07H 19/06* (2006.01)
*C07H 19/16* (2006.01)

(52) U.S. Cl. .................. 536/23.1; 536/26.7; 536/26.81; 536/26.9; 536/27.27; 536/28.4

(58) Field of Classification Search ................ 536/23.1, 536/26.7, 26.81, 26.9, 27.27, 28.4
See application file for complete search history.

(56) References Cited

U.S. PATENT DOCUMENTS 6,268,490 B1 * 7/2001 Imanishi et al. ........... 536/23.1

OTHER PUBLICATIONS

Yoon et al., Elucidation of the sequence–specific thirdstrand recognition of four Watson–crick base pairs in a pyrimidine triple–helix motif: T•AT, C•GC, T•G, and G•TA. *Proc. Natl. Acad. Sci. USA*, 89:3840–3844 (1992).

Povsic et al., Triple helix formation by oligonucleotides on DNA extended to the physiological pH range, *J. Am. Chem. Soc.*, 111(8):3059–3061 (1989).

Chan et al., Triplex DNA: fundamentals, advances, and potential applications for gene therapy, *J. Mol. Med.*, 75:267–282 (1997).

* cited by examiner

*Primary Examiner*—James O. Wilson
*Assistant Examiner*—Howard V. Owens
(74) *Attorney, Agent, or Firm*—Browdy and Neimark, P.L.L.C.

(57) ABSTRACT

Nucleoside analogues expressed by the following general formula

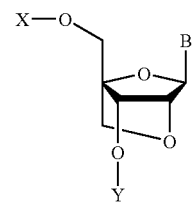

where B represents an aromatic base having carbonyl oxygen at the 2-position, or a 2-hydroxyphenyl group, or oligonucleotide derivatives containing one or more of the nucleoside analogues are provided.

The oligonucleotide derivatives are triplex-forming oligonucleotide derivatives which bind specifically to target double-stranded DNA with high affinity in the antigene method to form triplexes, and can thereby control and inhibit the expression of relevant genes efficiently, and which show high resistance to nucleases.

10 Claims, No Drawings

NUCLEOSIDE ANALOGS AND OLIGONUCLEOTIDE DERIVATIVES CONTAINING THESE ANALOGS

TECHNICAL FIELD

This invention relates to novel nucleoside analogues and nucleotide analogues, and further to poly- or oligonucleotide derivatives containing the nucleotide analogues, and more specifically to triplex-forming poly- or oligonucleotide derivatives suitable for the antigene method.

BACKGROUND ART

In 1978, it was reported for the first time that an antisense molecule inhibited infection with influenza virus. Then, reports that antisense molecules inhibited oncogene expression and AIDS infection were also made. Since antisense oligonucleotides specifically control the expression of undesirable genes, they are one of the fields that have been expected most as pharmaceuticals in recent years.

The antisense method is based on the concept that in a series of steps during flow according to the so-called central dogma, DNA→mRNA→protein, the process of translation from MRNA to protein is to be controlled with the use an antisense oligonucleotide complementary to mRNA.

However, when a native oligonucleotide is applied to this method as an antisense molecule, there have been problems that it is degraded by various in vivo nucleases, or its permeation through the cell membrane is not high. Therefore, the inventors of the present invention performed the synthesis of a nucleoside analogue unit which has the following general formula

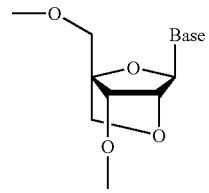

where Base represents a purine or pyrimidine nucleic acid base or its modification product, and in which the conformation of the sugar moiety has been fixed. They found that oligonucleotide derivatives prepared with the use of the nucleoside analogue unit are useful as antisense molecules, and they filed a patent application covering the oligonucleotide derivatives (Japanese Unexamined Patent Publication No. 1998-304889).

On the other hand, a method which comprises targeting double-stranded gene DNA, and effecting direct binding to the double-stranded DNA to form a triplex, thereby suppressing transcription to mRNA is called the antigene method. With the antigene method, it is known that triplex-forming oligonucleotides (TFO's) used as antigene molecules bind to the homopurine tract in double-stranded DNA via Hoogsteen hydrogen bonding or reverse Hoogsteen hydrogen bonding. Generally, the former mode of bonding is widely used (P. P. Chan and P. M. Glazer, J. Mol. Med., 75, 267–282(1997)).

Chemical formulas illustrating typical examples of the modes of bonding for triplex-forming Hoogsteen bonding and reverse Hoogsteen bonding are shown below.

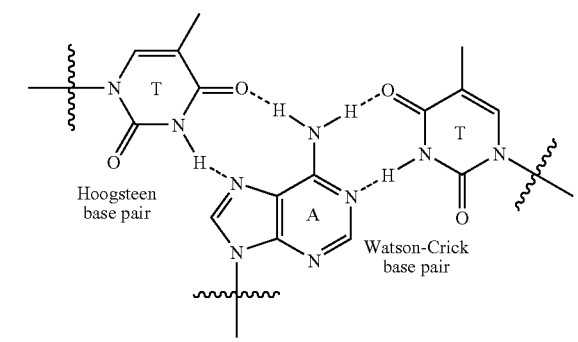

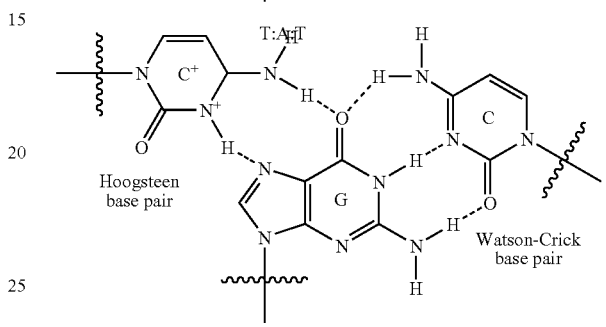

C⁺:G:C

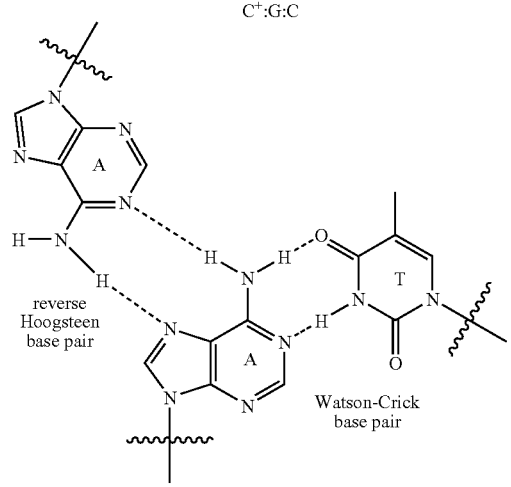

A:A:T

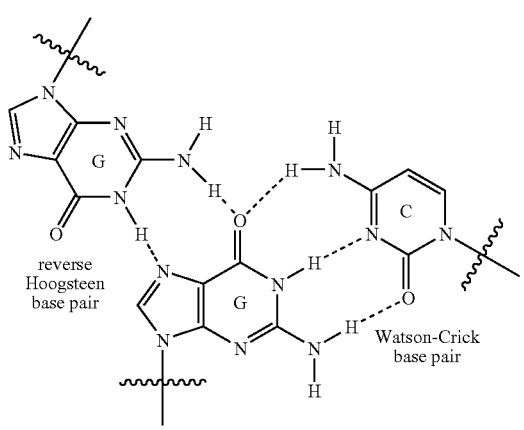

G:G:C where the two modes of bonding represented by a are T:A:T and C+:G:C bondings which are Hoogsteen bondings, while the two modes of bonding represented by b are A:T:A and G:G:C bondings which are reverse Hoogsteen bondings.

According to these modes of bonding, thymine is hydrogen-bonded to adenine of an AT base pair, and cytosine having the nitrogen atom at the 3-position protonated is hydrogen-bonded to guanine of a GC base pair. That is, the nitrogen atom at the 3-position of the cytosine base in an oligonucleotide has to be protonated in order to recognize a duplex containing a GC base pair and form a stable triplex. Thus, the triplex is stabilized under acidic conditions, but the triplex-forming ability is not sufficient in the in vivo pH range. Various other problems for the formation of a stable triplex remain to be solved, such that the targeted sequence is limited to the homopurine tract.

To solve these problems, numerous triplex-forming nucleoside analogues have been reported. Of them, the analogue methylated at the 5-position of cytosine (5-methylcytosine) is known to recognize a GC base pair specifically, enhancing a triplex-forming ability. Thus, this analogue has been widely used in conventional triplex-forming oligonucleotides (T. J. Povsic and P. B. Dervan, J. Am. Chem. Soc., 111, 3059–3061(1989)).

However, if a pyrimidine base is present in a homopurine tract, the target sequence of double-stranded DNA, the stability of the resulting triplex markedly. decreases, and this poses a serious problem in the antigene method. In this connection, T, a native nucleic acid base, has been reported to be capable of recognizing a CG base pair (Yoon, K. et al., (1992) Proc. Natl. Acad. Sci. USA, 89, 3840–3844). However, its ability is not satisfactory for practical use, and there has been a demand for the development of an oligonucleotide derivative which can specifically recognize a CG base pair present in a homopurine tract and has a high triplex-forming ability.

DISCLOSURE OF THE INVENTION

The present invention aims to provide a triplex-forming oligonucleotide molecule for antigene purposes which binds specifically to target double-stranded DNA with high affinity and can thereby control the expression of a particular gene with high efficiency. The invention aims, particularly, at synthesizing nucleotide analogues which specifically recognize a CG base pair or a TA base pair present in a target sequence, and bind to the base pair with high affinity to form a triplex, and providing triplex-forming oligo- or polynucleotide derivatives containing the analogues.

According to this invention, there have been synthesized bicyclic nucleoside (bicyclonucleoside) analogues of the following general formula

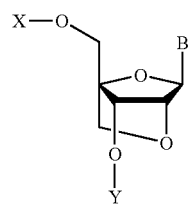

where B is a substituent selected from substituents expressed by the following general formulas

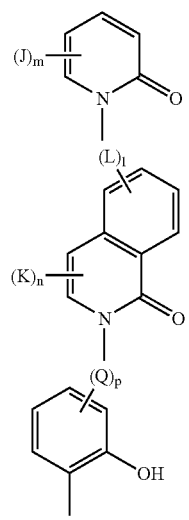

where J, K, L and Q are identical or different, and each denote —H, a lower alkyl, —OH, or —NH$_2$, 1, m and p independently denote an integer of 1 to 4, and n denotes an integer of 1 or 2, X and Y are identical or different, and each represent hydrogen, an alkyl group, an alkenyl group, an alkinyl group, a cycloalkyl group, an aralkyl group, an aryl group, an acyl group, or a silyl group, the bicyclonucleoside analogues using in the nucleic acid base moiety an aromatic base having carbonyl oxygen at the 2-position, such as 2-oxypyridyl, or using substituted or unsubstituted 2-hydroxylphenyl instead of the nucleic acid base, and having the conformation of the sugar moiety fixed; or amidite derivatives of the bicyclonucleoside analogues. Further, triplex-forming oligonucleotide derivatives have been synthesized using the bicyclonucleoside analogues or amidite derivatives.

It has been confirmed that the oligonucleotide derivatives of the present invention are very useful as TFO's which specifically recognize double-stranded DNA containing a CG base pair or a TA base pair and form a stable triplex. Details of the present invention will be offered below.

EMBODIMENTS OF THE INVENTION

The nucleoside analogues of the present invention can be synthesized by reactions shown below. To facilitate explanation, a synthetic example of a nucleoside analogue having 2-oxopyridyl as the nucleic acid base moiety is shown. However, those analogues using other bases, such as substituted or unsubstituted 2-oxopyridyl or substituted or unsubstituted isoquinoline, which are included in the present invention, can also be synthesized in the same manner according to the following reaction scheme:

Scheme 1

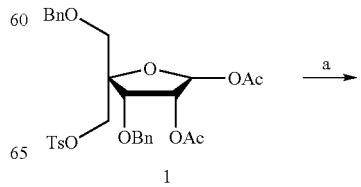

1

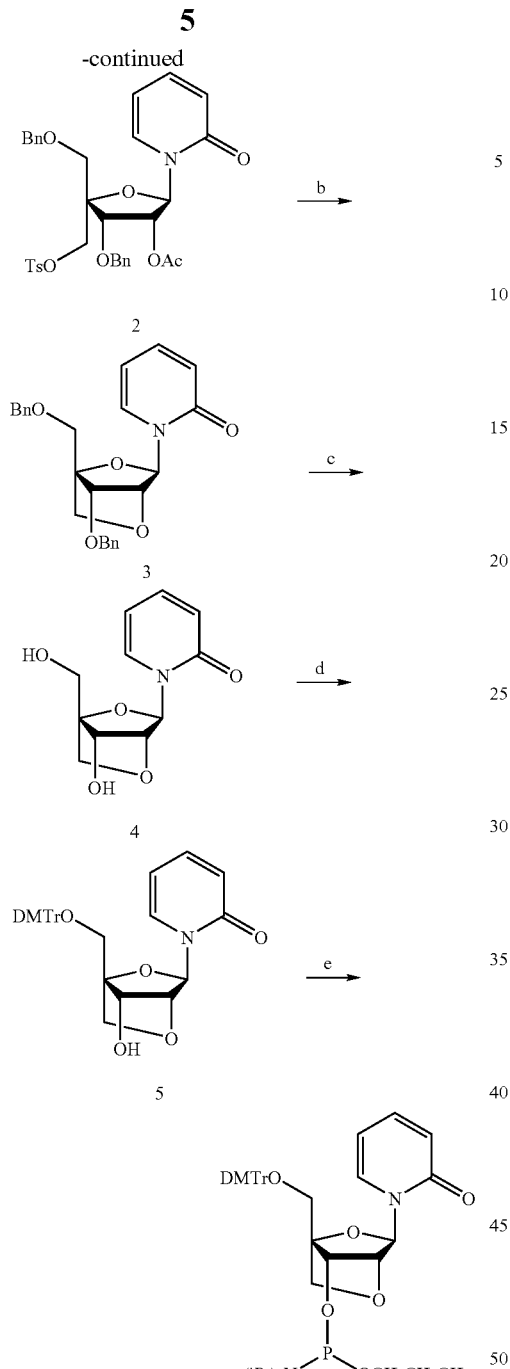

Reagents and Condition.
(a) pyridin-2-one, BSA, TMSOTf, dichloroethane, reflux, 74%;
(b) K$_2$CO$_3$, MeOH, rt, %;
(c) 20% Pd(OH)$_2$—C, cyclohexene, EtOH, reflux, 95%;
(d) DMTrCl pyridine, rt, 96%;
(e) 2-cyanoethyl N,N,N′, N′-isopropylphorodiamidite, diisopropylammonium tetrazolide, MeCN—THF, rt, 98%.

Starting compound 1 can be easily produced from D-glucose. This compound 1 is treated with 2-oxopyridine, N,O-bis(trimethylsilyl)acetamide (BSA), and trimethylsilyl-trifluoromethane sulfonate (TMSOTf) in dichloromethane to obtain compound 2. This compound 2 is brought into contact with potassium bicarbonate in methanol to obtain bicyclonucleoside 3. Then, the bicyclonucleoside 3 is subjected to hydrogenolysis to obtain the desired nucleoside analogue (compound 4).

Phosphoroamidate (compound 6), a constituent unit suitable for DNA synthesis, is obtained in the following manner: Compound 5 is derived from compound 4 by dimethoxytritylation, and is then phosphytylated to obtain compound 6.

This compound 6 and native nucleoside amidite compounds are combined to synthesize various oligonucleotide analogues with the use of an automated DNA synthesizer. The synthesized crude products are purified using an oligopack and a reverse phase chromatographic column. The purity of the purified products is confirmed by HPLC analysis, and the final products can be identified by MALDI-MS.

Synthetic examples of nucleoside analogues having 2-hydroxypheny as the nucleic acid base moiety are also shown. The method of synthesis involved here can also be applied to nucleoside analogues having substituted 2-hydroxpyphenyl that are included in the present invention.

Scheme 1

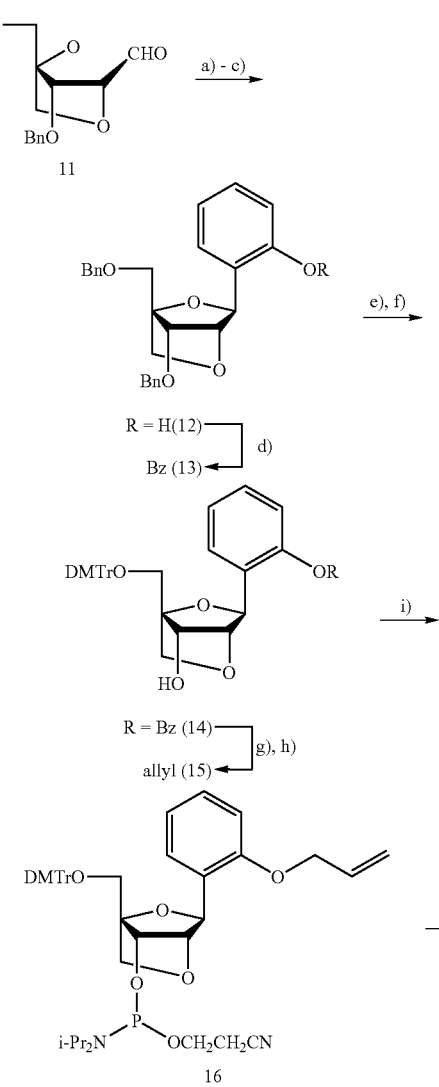

-continued

5'-TTTTTCT(HB<sup>B</sup>)TCTCTC-3'

TFO I (X = HB<sup>B</sup>)

C:2'-deoxy-5-methylcytidine

Reagents and conditions:
a) 2-allyloxyphenylmagnesium bromide, THF, rt, 1h;
b) TMAD, Ph$_3$P, rt, 15 h;
c) NaBH$_4$, Pd(Ph$_3$P)$_4$, THF, rt, 8 h (42%, 3 steps from 1);
d) BzCl, Et$_3$N, CH$_2$Cl$_2$, rt, 0.5 h (90%);
e) 20% Pd(OH)$_2$-C, cyclohexene, EtOH, reflux, 2 h (85%);
f) DMTrCl, pyridine, rt, 3 h (94%);
g) K$_2$CO$_3$, MeOH, rt, 5 min (97%);
h) allyl bromide, K$_2$CO$_3$, acetone, rt, 40 h (87%);
i) (i-Pr$_2$N$_2$)POCH$_2$CH$_2$CN, diisopropylammonium tetrazolide, MeCN-THF, rt, 4 h (81%);
j) DNA synthesis.

The starting material (11) is treated with a magnesium salt of 2-hydroxyphenyl in THF, and then the resulting bound compound is subjected to Mitsunobu reaction. Then, the compound is deallylated to obtain a bicyclonucleoside (12) (yield 42%). Then, the compound (12) is treated with benzoyl chloride (BzCl) in pyridine to obtain compound (13) (yield 90%). Then, the compound (13) is subjected to hydrogenolysis, and further dimethoxytritylated to obtain compound (14) in a yield of 80%.

The benzoyl group of the compound (14) is converted into an allyl group to obtain compound (15). Phosphoroamidite (16), a construction block preferred for DNA synthesis, is obtained by phosphytylation (16) (yield 81%). Then, the phosphoroamidite (16) can be incorporated into a triplex-forming oligonucleotide or polynucleotide derivative according to a standard phosphoroamidite protocol with the use of an automated DNA synthesizer. The allyl protective group in the hydroxyphenyl moiety is eliminated by treatment with NaBH$_4$ and Pd(PPh$_3$)$_4$ to obtain the desired triplex-forming oligonucleotide (TFOI).

The oligonucleoside analogues of the present invention can be rendered existent at one or more of or at all of those positions, in an oligonucleotide or polynucleotide derivative forming a triplex together with double-stranded DNA via hydrogen bonding, which correspond to CG base pairs or TA base pairs of the target double-stranded DNA. Among the oligonucleotide or polynucleotide derivatives of the present invention are included those in which portions other than the nucleoside analogues of the present invention are native nucleosides, and those containing one or more of nucleoside analogues whose sugar moiety has the same structure as the nucleoside analogue of the present invention and whose base moiety is a native nucleic acid base.

According to the present invention, there can be synthesized an antisense molecule having a necessary number (length) of the nucleoside analogues of the present invention introduced at the necessary positions. The entire length of the oligonucleotide derivative is 2 to 50, preferably 10 to 30, of the nucleoside units.

Such oligonucleotide derivatives (TFO's) are minimally decomposed by various nucleases, and can persist in vivo for a long time after administration to the living organism. Then, the TFO's form a stable triplex together with double-stranded DNA, and inhibit transcription to messenger RNA, and for example, can inhibit the biosynthesis of an etiologic protein.

The nucleoside analogues of the present invention make it possible to specifically recognize the CG base pair or TA base pair of target double-stranded DNA thus far difficult to recognize. Hence, they enable the formation of triplexes by targeting double-stranded DNA with any sequences.

In connection with the triplex-forming ability of the oligonucleotide derivatives of the present invention, the melting temperature (Tm value) was measured as in the case of a duplex, as will be explained in Experimental Examples to be offered later. When a triplex is to dissociate, a Hoogsteen bond with a low bond strength breaks first, and then a Watson-Crick bond with a relatively high bond strength breaks. Thus, transitions in two stages are generally observed during the increase of the ultraviolet absorption intensity. The mid-point of the transition observed first was taken as the melting temperature involved when the third strand was dissociated, and the triplex-forming ability was evaluated based on this measurement of the melting temperature.

In view of these facts, the oligonucleotide derivatives (TFO's) using the nucleoside analogues of the present invention are expected to be useful as pharmaceuticals, including antineoplastics and antivirals, for inhibiting the actions of particular genes and treating diseases. If desired, vehicles, tonicity agents, solution adjuvants, stabilizers, antiseptics, and soothing agents are added, whereby the TFO's can be converted into tablets, powders, granules, capsules, liposome capsules, injections, liquids and solutions, nasal drops, etc., and further into lyophilization products. They can be prepared by the customary methods.

The oligonucleotide derivatives of the present invention are directly applied to the affected site of a patient, or are applied to a patient by administration into the blood vessel so that the compounds can arrive at the affected site. Furthermore, oligonucleotide-encapsulating materials, which enhance persistence and membrane permeation, can be used. For example, liposome, poly-L-lysine, lipid, cholesterol, lipofectin or their analogues can be named.

The dose of the oligonucleotide derivative of the present invention can be adjusted, as desired, according to the condition, age, sex, body weight, and so on of patients, and the oligonucleotide derivatives can be used in preferred amounts. The mode of their administration depends on the condition of patients, and dosage forms for them, and preferred methods can be used from among various modes of administration, such as oral administration, intramuscular administration, intraperitoneal administration, intradermal administration, subcutaneous administration, intravenous administration, intraarterial administration, and rectal administration. As preparations for topical administration, the oligonucleotide derivatives of the present invention can be formed into ointments, creams, liquids and solutions, or plasters by blending them with pharmaceutical carriers in customary use.

When the oligonucleotide or polynucleotide derivatives of the present invention are used as probes or markers, they can be used for detection of double-stranded DNA having particular nucleic acid sequences. In this case, fluorescence-labeled TFO's can be used.

The synthesis and properties of the nucleoside analogues of the present invention and the oligonucleotide derivatives using the nucleoside analogues will be described in further detail by Examples and Experimental Examples.

EXAMPLE 1

Synthesis of Nucleoside Analogues
(1) Synthesis of 1-[2-O-acetyl-3,5-O-dibenzyl-4-(p-toluenesulfonyloxymethyl)-β-D-ribofuranosyl]-2-oxopyridine (Compound 2)

In a stream of nitrogen, pyridin-2-one (52 mg, 0.52 mmol) and N,O-bistrimethylsilylacetamide (0.16 ml, 0.57 mmol)

were added to an anhydrous dichloroethane solution (4 ml) of compound 1 (154 mg, 0.26 mmol), and the mixture was heated under reflux for 2 hours. Under cooling with ice, trimethylsilyltrifuoromethane sulfonate (0.051 ml, 0.28 mmol) was added, and the mixture was heated under reflux for 4 hours. After a saturated aqueous solution of sodium bicarbonate was added to the reaction solution, the system was extracted with ethyl acetate. The organic layer was washed with water and a saturated aqueous solution of sodium chloride, and then dried over anhydrous sodium sulfate. The solvent was distilled off under reduced pressure, and the resulting crude product was purified by silica gel column chromatography (AcOEt-n-hexane, 1:1) to obtain compound 2 (169 mg, 74%).

Colorless oily substance. $[\alpha]_D^{26}$+55.9°(c 1.00, CHCl$_3$). IR$\nu_{max}$ (KBr): 1748, 1667, 1591, 1363, 1229, 1180, 1111 cm$^{-1}$. $^1$H-NMR (CDCl$_3$) δ: 2.03 (3H, s), 2.42(3H, s), 3.54, 3.83 (2H, AB, J=10 Hz), 4.17, 4.27 (2H, AB, J=11 Hz),4.34, 4.53 (2H, AB, J=12 Hz), 4.38, 4.45 (2H, AB, J=11 Hz), 4.45 (1H,d, J=6 Hz), 5.37 (1H, dd, J=3, 6 Hz), 5.83 (1H, dt, J=1, 7 Hz), 6.00(1H, d, J=3 Hz), 6.43 (1H, d, J=9 Hz),7.18–7.38 (13H, m), 7.65 (1H, dd,J=2, 7 Hz), 7.75 (2H, d, J=8 Hz). $^{13}$C-NMR (CDCl$_3$) δ$_c$: 20.77, 21.72, 69.42, 69.74, 73.53, 74.15, 75.03, 76.64, 85.48, 88.63, 105.67. 120.41,120.74, 127.86, 127.95, 128.00, 128.32, 128.35, 129.67, 133.31, 136.93,137.05, 144.94, 161.78, 169.26. Mass (EI): m/z 663 (M$^+$, 3.9), 91 (100). Anal. Calcd. for C$_{34}$H$_{35}$NO$_9$S: C, 64.44; H, 5.57; N, 2.21; S, 5.06. Found:C, 64.25; H, 5.56; N, 2.18; S, 4.94.

(2) Synthesis of 1-(3,5-O-dibenzyl-2-O,4-C-methylene-β-D-ribofuranosyl)-2-oxopyridine (Compound 3)

Potassium carbonate (72 mg, 0.52 mmol) was added to a methanol solution (3 ml) of compound 2 (110 mg, 0.17 mmol), and the mixture was stirred for 17 hours at room temperature. The reaction solution was distilled under reduced pressure, then water was added, and the mixture was extracted with ethyl acetate. The organic layer was washed with water and a saturated aqueous solution of sodium chloride, and then dried over anhydrous sodium sulfate. The solvent was distilled off under reduced pressure, and the resulting crude product was purified by silica gel column chromatography (AcOEt-n-hexane, 2:3 to 2:1) to obtain compound 3 (73 mg, quant.).

White powder. mp 117–118° C. $[\alpha]_D^{26}$+202.9° (c 1.00, CHCl$_3$). IR$\nu_{max}$ (KBr): 1661, 1584 cm$^{-1}$. $^1$H-NMR (CDCl$_3$) δ: 3.84, 3.86 (2H, AB, J=11 Hz), 3.90,4.05 (2H, AB, J=8 Hz), 3.97 (1H, s), 4.44, 4.59 (2H, AB, J=12 Hz),4.63, 4.65 (2H, AB, J=12 Hz), 4.67 (1H, s), 5.90 (1H, s), 6.10 (1H, dt, J=1, 7 Hz), 6.51 (1H, d, J=9 Hz), 7.20–7.39 (11H, m), 7.79 (1H, dd, J=2, 7 Hz). $^{13}$C-NMR (CDCl$_3$) δ$_c$: 64.69, 72.04, 72.15, 73.60, 75.60, 76.29, 87.18, 88.00, 105.64, 120.30, 127.31, 127.53, 127.73, 127.83, 128.27, 128.35,128.35, 132.03, 136.84, 137.53, 139.50, 161.78. Mass (EI): m/z 419 (M$^+$,10.4), 91 (100). Anal. Calcd. for C$_{25}$H$_{25}$NO$_5$: C, 71.58; H, 6.01; N, 3.34. Found: C, 71.53; H, 6.03; N, 3.37.

(3) Synthesis of 1-(2-O,4-C-methylene-β-D-ribofuranosyl)-2-oxopyridine (Compound 4)

To an ethanol solution (2 ml) of compound 3 (68 mg, 0.16 mmol), 20% palladium hydroxide carbon (60 mg) and cyclohexene (0.82 ml, 8.10 mmols) were added, and the mixture was heated under reflux for 1.5 hours. The reaction solution was filtered, and silica gel (0.2 g) was added to the filtrate, followed by distilling off the solvent under reduced pressure. The resulting crude product was purified by silica gel column chromatography (CHCl$_3$-MeOH, 20:1) to obtain compound 4 (37 mg, 95%). The compound was partially recrystallized from acetone.

Colorless plate-like crystals. mp 206–207° C.(acetone). $[\alpha]_D^{26}$+162.8° (c 1.00, CH$_3$OH). IR$\nu_{max}$ (KBr): 3293, 2952, 1655, 1567, 1051 cm$^{-1}$. $^1$H-NMR (CD$_3$OD) δ: 3.94 (2H,s), 3.82, 3.99 (2H, AB, J=8 Hz), 4.04 (1H, s), 4.33 (1H, s), 5.79 (1H,s), 6.45–6.53 (2H, m), 7.53–7.59 (1H, m), 8.01 (1H, dd, J=1, 7 Hz).$^{13}$C-NMR (CD$_3$OD) δ$_c$: 57.76, 69.92, 72.49, 80.59, 89.09, 90.42, 108.10, 120.24, 133.68, 142.15, 163.83. Mass (EI): m/z 239 (M$^+$, 30.3), 96 (100). Anal. Calcd. for C$_{11}$H$_{13}$NO$_5$: C, 55.23; H, 5.48; N, 5.86. Found: C, 55.05; H, 5.44; N, 5.82.

(4) Synthesis of 1-[5-O-(4,4'-dimethoxytrityl)-2-O,4-C-methylene-β-D-ribofuranosyl]-2-oxopyridine (Compound 5)

In a stream of nitrogen, dimethoxytrityl chloride (113 mg, 0.33 mmol) was added at room temperature to a pyridine solution (1 ml) of compound 4 (50 mg, 0.21 mmol), and the mixture was stirred for 1 hour. A saturated aqueous solution of sodium bicarbonate was added to the reaction solution, and the mixture was extracted with ethyl acetate. The organic layer was washed with water and a saturated aqueous solution of sodium chloride, and then dried over anhydrous sodium sulfate. The solvent was distilled off under reduced pressure, and the resulting crude product was purified by silica gel column chromatography (AcOEt-n-hexane-Et$_3$N, 100:20:1) to obtain compound 5 (109 mg, 96%).

White powder. mp 114–115° C. $[\alpha]_D^{26}$+56.5° (c 1.00, CHCl$_3$). IR$\nu_{max}$ (KBr): 3279, 2952, 1657, 2574, 1508, 1252 cm$^{-1}$. $^1$H-NMR (acetone-d$_6$) δ: 3.52, 3.59(2H, AB, J=11 Hz), 3.80-3.82 (7H, m), 3.94 (1H, d, J=8 Hz), 4.34 (1H,s), 4.38 (1H, d, J=5 Hz), 4.78 (1H, d, J=5 Hz), 5.77 (1H, s), 6.23 (1H,s), 6.38 (1H, d, J=9 Hz), 6.92 (4H, d, J=8 Hz), 7.26–7.56 (10H, m),8.07 (1H, dd, J=2, 7 Hz). $^{13}$C-NMR (acetone-d$_6$) δ$_c$: 55.40, 59.44, 70.15, 72.30, 79.78, 87.06, 88.48, 88.56, 105.70, 105.72, 113.76, 120.54, 127.48,128.46, 128.74, 130.75, 130.77, 136.19, 136.39, 140.36, 140.38, 145.71, 159.40, 161.85. Mass (EI): m/z 303 (DMTr, 100). Anal. Calcd. for C$_{32}$H$_{31}$NO$_7$·½ H$_2$O: C, 69.81; H, 5.86; N, 2.54. Found: C, 69.90; H, 5.78; N, 2.55.

(5) Synthesis of 1-[3-O-[2-cyanoethoxy(diisopropylamino) phosphino]-5-O-(4,4'-dimethoxytrityl)-2-O,4-C-methylene-β-D-ribofuranosyl]-2-oxopyridine (Compound 6)

In a stream of nitrogen, 2-cyanoethyl-N,N,N',N'-tetraisopropylphosphorodiamidite (52 μl, 0.16 mmol) was added dropwise at room temperature to an anhydrous acetonitrile-tetrahydrofuran solution (3:1, 0.8 ml) of compound 5 (20 mg, 0.037 mmol) and diisopropylammonium tetrazolide (17 mg, 0.098 mmol), and the mixture was stirred for 9 hours. After the solvents were distilled off, the residue was purified by flash silica gel column chromatography (AcOEt-n-hexane-Et$_3$N, 50:50:1) to obtain compound 6 (26 mg, 95%).

White powder. mp 68–69° C. $^{31}$P-NMR (CDCl$_3$) δ: 148.75, 149.35.

EXAMPLES 2 TO 4

(1) to (3) of Example 1 were repeated using isoquinolin-1-one, 5-methyl-2-oxopyridine (Barash, M.; Osbond, J. M. Wikens, J. C. J. C. S. 1959, 3530), or 4-hydroxy-2-oxopyridine instead of 2-oxopyridine, thereby synthesizing 2-(2-O,4-C-methylene-β-D-ribofuranosyl)isoquinolin-1-one, 1-(2-O,4-C-methylene-β-D-ribofuranosyl]-5-methyl-2-oxopyridine, and 1-(2-O,4-C-methylene-β-D-ribofuranosyl)-4-hydroxy-2-oxopyridine (compounds corresponding to compound 4 of Example 1).

When 4-hydroxy-2-oxopyridine was used as the starting material, the steps (1) and (2) of Example 1 were performed without protecting the hydroxyl group at the 4-position, and a benzoyl group was used for protection in the step (3).

For these compounds, (4) and (5) of Example 1 were repeated, thereby synthesizing their respective amidite compounds (compounds corresponding to compound 6 of Example 1).

EXAMPLE 5

General Synthesis of Oligonucleotide Derivatives

Synthesis of oligomers was performed on a scale of 0.2 μmol by Pharmacia's DNA synthesizer, Gene Assembler Plus. The concentrations of solvents, reagents and phosphoroamidites are the same as in the case of native DNA synthesis. The DMTr group of 5'-O-DMTr-thymidine (0.2 pmol) having a 3'-hydroxyl group bonded to a CPG substrate was deprotected with trichloroacetic acid. For the 5'-hydroxyl group, condensation reaction was performed repeatedly using an amidite comprising 4 nucleic acid bases for native DNA synthesis and the amidites of the present invention (compound 6 of Example 1(5), or compounds of Examples 2 to 4). As a result, oligonucleotide derivatives having the respective sequences were synthesized. The synthetic cycle is as described below.

Synthetic Cycle (0.2 μmol Scale)

1) Detritylation, 1% CCl$_3$COOH in CH$_2$ClCH$_2$Cl, 6 sec
2) Coupling, 0.1 M phosphoramidite (25 equiv.), 0.5 M 1H-tetrazole (500 equiv.) in MeCN, 2 min
3) Capping, 3% 4-(dimethylamino)pyridine, 10% Ac$_2$O, in MeCN, 18 sec
4) Oxidation, 0.01 M I$_2$ in 2,4,6-collidine/H$_2$O/MeCN (1:5:11), 6 sec After synthesis, the oligomer was cut out of the substrate by treatment with concentrated aqueous ammonia by the customary method. Also, the protective group, cyanoethyl group, on the phosphorus atom was eliminated, and the protective groups for adenine, guanine and cytosine were removed.

The resulting 5'-O-DMTr-converted oligonucleotide analogues were rid of the DMTr group by 5 ml of trifluoroacetic acid on a reverse phase column chromatograph (NENT Life Science Products, NENSORB™ PREP), and further purified to obtain the intended oligonucleotide analogues.

In Examples 6 and 7 offered below, the synthesis of 2-hydroxyphenyl-containing nucleoside analogues and nucleotide derivatives containing them will be described. The path of synthesis is shown in the following reaction scheme:

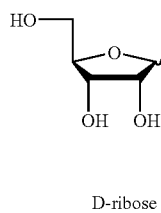

D-ribose

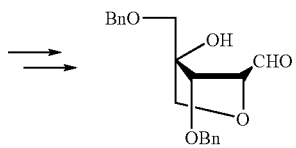

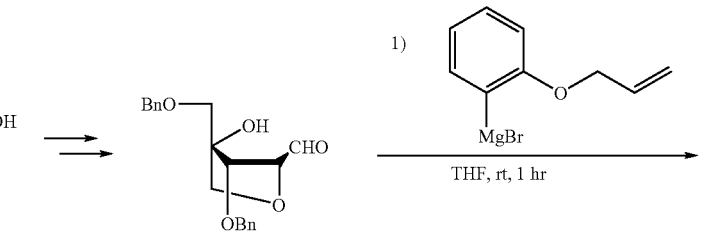

21

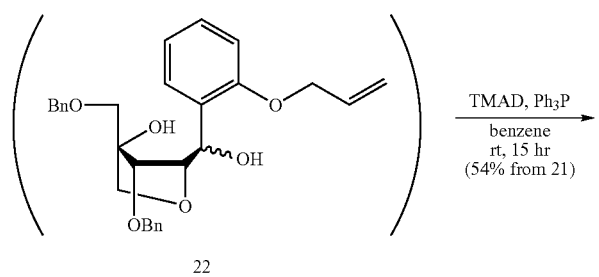

22

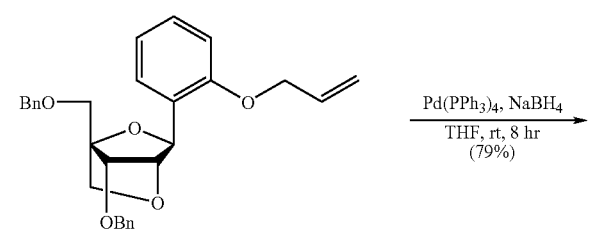

23

-continued
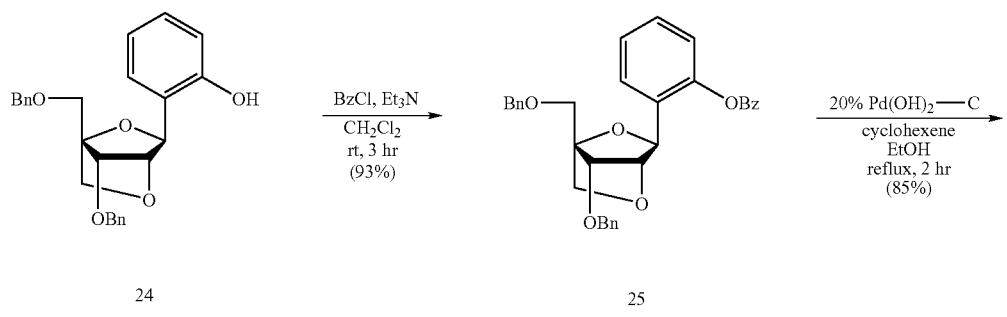
1) T. Imanishi et al., *Tetrahedron Lett.*, 41, 215 (2000).
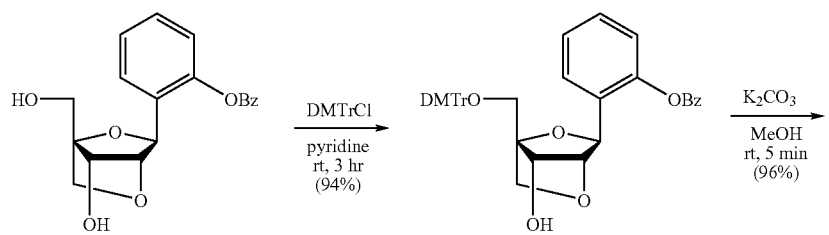
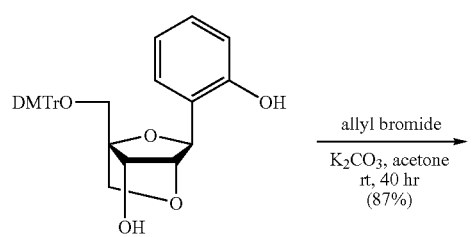
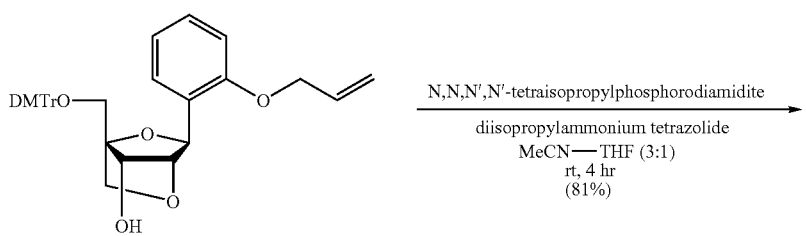

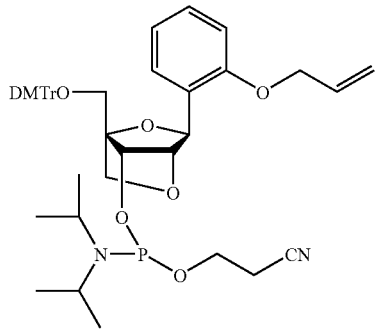

30

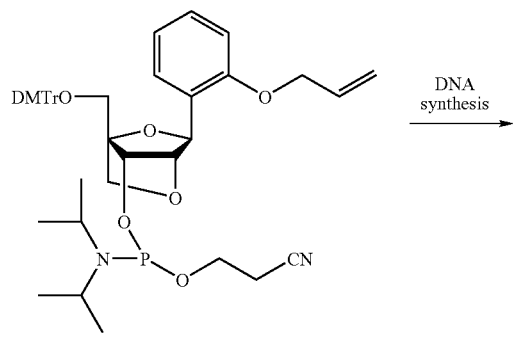

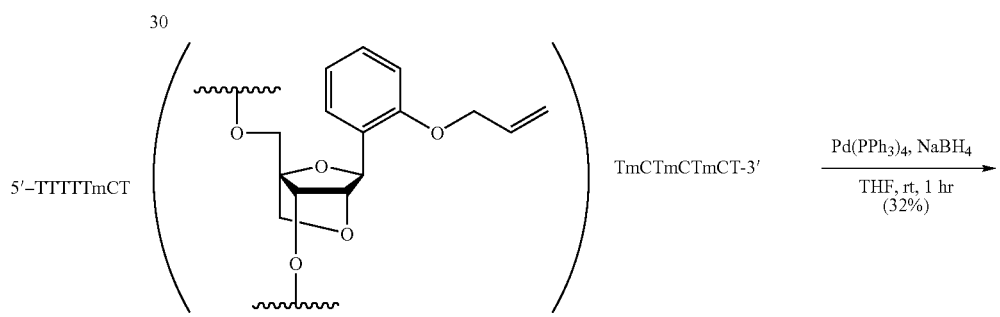

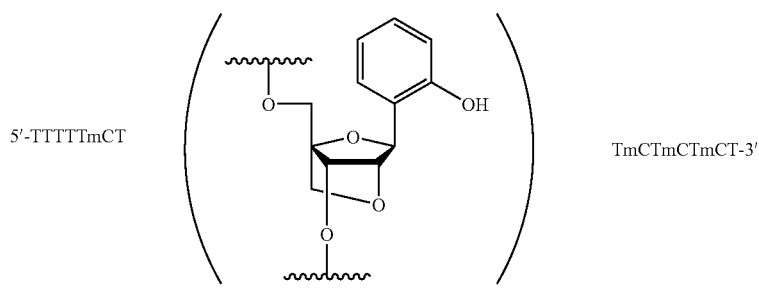

EXAMPLE 6

Synthesis of 2-hydroxyphenyl-Containing Nucleoside Analogue (1) Synthesis of 1-allyloxy-2-(3,5-O-dibenzyl-2-O,4-C-methylene-β-D-ribofuranosyl)benzene (23)

In a stream of nitrogen, an anhydrous tetrahydrofuran (30 ml) solution of a compound (21)1) known in the literature (1.46 g, 4.3 mmols) was added dropwise to an anhydrous tetrahydrofuran (70 ml) solution of 2-allyloxyphenylmagnesium bromide (15 mmols), and the mixture was stirred for 1 hour at room temperature. After water was added to the reaction solution, the system was extracted with ethyl acetate 3 times. The organic layer was washed with water and a saturated aqueous solution of sodium chloride, and then dried over anhydrous sodium sulfate. The solvent was distilled off under reduced pressure, and the resulting crude product was purified by silica gel column chromatography (n-hexane:ethyl acetate=3:1) to obtain a colorless oily substance (22) (1.40 g, 68%). N,N,N',N'-tetramethylazodicarboxyamide (0.76 g, 4.4 mmols) and triphenylphosphine (1.16 g, 4.4 mmols) were added to an anhydrous benzene (30 ml) solution of compound 2, and the mixture was stirred for 15 hours at room temperature. After the reaction solution was distilled under reduced pressure, the residue was purified by silica gel column chromatography (n-hexane:ethyl acetate=9:1) to obtain a white powder (23) (1.05 g, 54% from 1)).

mp 60–63° C. IR$\nu_{max}$(KBr): 2928, 1489, 1104 cm$^{-1}$. $^1$H-NMR (CDCl$_3$) δ: 3.88, 3.89 (2H, AB, J=12 Hz), 4.02 (1H, s), 4.08, 4.11 (2H, AB, J=7 Hz), 4.01 (1H, s), 4.01, 4.52 (2H, AB, J=12 Hz), 4.55–4.59 (2H, m), 4.68 (2H, s), 5.28 (1H, dd, J=11, 1 Hz), 5.35 (1H, s), 5.41 (1H, dd, J=17, 1 Hz), 5.96–6.10 (1H, m), 6.81 (1H, d, J=8 Hz), 6.94 (1H, dd, J=7, 8 Hz), 7.19–7.40 (11H, m), 7.53 (1H, d, J=7 Hz). $^{13}$C-NMR (CDCl$_3$) δ$_C$: 66.59, 71.91, 73.38, 73.64, 78.10, 79.07, 80.58, 85.51, 110.77, 117.10, 120.57, 126.79, 127.46, 127.52, 127.62, 128.21, 132.82, 137.60, 138.06, 154.25.

Cited Reference
1) T. Imanishi et al., *Tetrahedron Lett.*, 41, 215(2000).
(2) Synthesis of 2-(3,5-O-dibenzyl-2-O,4-C-methylene-β-D-ribofuranosyl)phenol (24)

Tetrakis(triphenylphosphine)palladium(0) (173 mg, 0.15 mmol) and sodium tetrahydroborate (260 mg, 6.9 mmols) were added to an anhydrous tetrahydrofuran (20 ml) solution of the compound (23) (1.05 g, 2.3 mmols), and the mixture was stirred for 8 hours at room temperature. After 1N hydrochloric acid was added, the system was extracted with ethyl acetate 3 times. The organic layer was washed with water and a saturated aqueous solution of sodium chloride, and then dried over anhydrous sodium sulfate. The solvent was distilled off under reduced pressure, and the resulting crude product was purified by silica gel column chromatography (n-hexane:ethyl acetate=4:1) to obtain colorless crystals (24) (755 mg, 79%).

mp 128–131° C. IR$\nu_{max}$(KBr): 3302, 1456, 1099 cm$^{-1}$. $^1$H-NMR (CDCl$_3$) δ: 3.72 (2H, s), 3.97, 4.04 (2H, AB, J=8 Hz), 4.31 (1H, s), 4.32 (1H, s), 4.49, 4.57 (2H, AB, J=11 Hz), 4.65, 4.67 (2H, AB, J=13 Hz), 5.41 (1H, s), 6.79–6.93 (3H, m), 7.11–7.36 (11H, m), 8.55 (1H, s). $^{13}$C-NMR (CDCl$_3$) δ C: 64.11, 72.29, 72.75, 73.58, 77.81, 82.12, 86.51, 118.03, 119.53, 120.47, 126.16, 127.53, 127.70, 127.75, 127.80, 128.26, 128.40, 128.92, 137.21, 137.26, 155.27.
(3) Synthesis of 1-benzoyloxy-2-(3,5-O-dibenzyl-2-O,4-C-methylene-β-D-ribofuranosyl)benzene (25)

Benzoyl chloride (0.06 ml, 0.52 mmol) and anhydrous triethylamine (0.073 ml, 0.52 mmol) were added to an anhydrous dichloromethane (3 ml) solution of the compound (24) (168 mg, 0.40 mmol), and the mixture was stirred for 3 hours at room temperature. After water was added to the reaction solution, the system was extracted with ethyl acetate 3 times. The organic layer was washed with water and a saturated aqueous solution of sodium chloride, and then dried over anhydrous sodium sulfate. The solvent was distilled off under reduced pressure, and the resulting crude product was purified by silica gel column chromatography (n-hexane:ethyl acetate=7:1) to obtain a colorless oily substance (25) (209 mg, 93%).

IR$\nu_{max}$(KBr): 2928, 1738, 1259 cm$^{-1}$. $^1$H-NMR (CDCl$_3$) δ: 3.86 (2H, s), 4.01, 4.06 (2H, AB, J=8 Hz), 4.08 (1H, s), 4.33 (1H, s), 4.44, 4.53 (2H, AB, J=12 Hz), 4.66, 4.67 (2H, AB, J=13 Hz), 5.28 (1H, s), 7.19–7.37 (15H, m), 7.52 (1H, dd, J=7, 7 Hz), 7.65 (1H, dd, J=7, 7 Hz), 8.18 (2H, d, J=7 Hz).
(4) Synthesis of 1-benzoyloxy-2-(2-O,4-C-methylene-β-D-ribofuranosyl)benzene (26)

In a stream of nitrogen, 20% palladium hydroxide-carbon (53 mg) and cyclohexene (0.52 ml, 5.1 mmols) were added to an anhydrous ethanol (2 ml) solution of the compound (25) (54 mg, 0.10 mmol), and the mixture was heated under reflux for 2 hours. After filtration, the solvent was distilled off under reduced pressure. The resulting crude product was purified by silica gel column chromatography (chloroform:methanol=80:3) to obtain a white powder (26) (30 mg, 85%).

mp 180–182° C. $^1$H-NMR (CD$_{3OD}$) δ: 3.87, 3.98 (2H, AB, J=8 Hz), 3.91, 3.93 (2H, AB, J=12 Hz), 4.13 (1H, s), 4.13 (1H, s), 5.11 (1H, s), 7.20–7.23 (1H, m), 7.32–7.41 (2H, m), 7.55–7.61 (2H, m), 7.69–7.74 (2H, m), 8.20 (2H, d, J=8 Hz). $^{13}$C-NMR (CD$_{3OD}$) δ C: 59.30, 71.51, 73.54, 80.89, 83.66, 88.28, 123.38, 127.16, 128.28, 129.59, 130.17, 130.96, 135.05, 148.46, 166.14.
(5) Synthesis of 1-benzoyloxy-2-[5-O-(4,4'-dimethoxytrityl)-(2-O,4-C-methylene-β-D-ribofuranosyl) benzene (27)

4,4'-dimethoxytrityl chloride (86 mg, 0.25 mmol) was added to an anhydrous pyridine (1 ml) solution of the compound (26) (58 mg, 0.17 mmol), and the mixture was stirred for 3 hours at room temperature. After water was added to the reaction solution, the system was extracted with ethyl acetate 3 times. The organic layer was washed with water and a saturated aqueous solution of sodium chloride, and then dried over anhydrous sodium sulfate. The solvent was distilled off under reduced pressure, and the resulting crude product was purified by silica gel column chromatography (n-hexane:ethyl acetate=2:1) to obtain a yellow powder (27) (121 mg, 94%).

mp 84–88° C. $^1$H-NMR (CDCl$_3$) δ: 1.87 (1H, d, J=6 Hz), 3.49, 3.54 (2H, AB, J=11 Hz), 3.80 (6H, s), 3.93, 3.99 (2H, AB, J=8 Hz), 4.26 (1H, s), 4.32 (1H, d, J=6 Hz), 5.27 (1H, s), 6.83–6.87 (4H, m), 7.22–7.83 (16H, m), 8.18–8.21 (2H, m).
(6) Synthesis of 2-[5-O-(4,4'-dimethoxytrityl)-2-O,4-C-methylene-β-D-ribofuranosyl)phenol (28)

Potassium carbonate (103 mg, 0.75 mmol) was added to an anhydrous methanol (5 ml) solution of the compound (27) (120 mg, 0.19 mmol), and the mixture was stirred for 5 minutes at room temperature. After the solvent was distilled off under reduced pressure, the residue was extracted with ethyl acetate 3 times. The organic layer was washed with water and a saturated aqueous solution of sodium chloride, and then dried over anhydrous sodium sulfate. The solvent was distilled off under reduced pressure, and the resulting crude product-was purified by silica gel column chromatography (n-hexane:ethyl acetate=3:2) to obtain a colorless oily substance (28) (96 mg, 96%).

$^1$H-NMR (CD$_3$COCD$_3$) δ: 3.44, 3.53 (2H, AB, J=11 Hz), 3.80 (6H, s), 3.96 (1H, s), 4.23 (1H, s), 4.27, 4.31 (2H, AB, J=5 Hz), 5.23 (1H, s), 6.85–6.92 (4H, m), 7.11–7.67 (13H, m), 8.02 (2H, d, J=7 Hz), 8.67 (1H, s).
(7) Synthesis of 1-allyloxy-2-[5-O-(4,4'-dimethoxytrityl)-2-O,4-C-methylene-β-D-ribofuranosyl)benzene (29)

Allyl bromide (0.017 ml, 0.20 mmol) was added to an anhydrous acetone (16 ml) solution of the compound (28) (96 mg, 0.18 mmol), whereafter potassium carbonate (27 mg, 0.20 mmol) was added, and the mixture was stirred for 40 hours at room temperature. After the solvent was distilled off under reduced pressure, the residue was extracted with ethyl acetate 3 times. The organic layer was washed with water and a saturated aqueous solution of sodium chloride, and then dried over anhydrous sodium sulfate. The solvent was distilled off under reduced pressure, and the resulting crude product was purified by silica gel column chromatography (n-hexane:ethyl acetate=3:1) to obtain a colorless oily substance (29) (90 mg, 87%).

$^{1}$H-NMR (CD$_{3}$COCD$_{3}$) δ: 3.45, 3.53 (2H, AB, J=11 Hz), 3.80 (6H, s), 3.96 (2H, s), 4.20 (1H, s), 4.24 (1H, d, J=5 Hz), 4.27 (1H, d, J=5 Hz), 4.67 (2H, m), 5.23 (1H, s), 5.28 (1H, dd, J=11, 1 Hz), 5.48 (1H, dd, J=17, 1 Hz), 6.12 (1H, m), 6.88–7.01 (6H, m), 7.24–7.36 (5H, m), 7.45 (3H, m), 7.60 (2H, d, J=7 Hz), 7.75 (1H, d, J=8 Hz).

(8) Synthesis of 1-allyloxy-2-[3-O-(N,N'-diisopropylamino-2-cyanoethoxyphosphino)-5–0-(4,4'-dimethoxytrityl)-2-O,4-C-methylene-β-D-ribofuranosyl)benzene (30)

N,N,N',N'-tetraisopropylphosphorodiamidite (0.064 ml, 0.20 mmol) was added into an anhydrous acetonitrile-tetrahydrofuran (3:1, 2 ml) solution of the compound (29) (69 mg, 0.12 mmol) and diisopropylammonium tetrazolide (24 mg, 0.12 mmol), and the mixture was stirred for 4 hours at room temperature. After the solvent was distilled off under reduced pressure, the residue was extracted with ethyl acetate 3 times. The organic layer was washed with water and a saturated aqueous solution of sodium chloride, and then dried over anhydrous sodium sulfate. The solvent was distilled off under reduced pressure, and the resulting crude product was purified by silica gel column chromatography (n-hexane:ethyl acetate=3:1) to obtain a white powder (30) (75 mg, 81%).

$^{13P}$-NMR (CD$_{3}$COCD$_{3}$) δ: 146.85, 147.73.

EXAMPLE 7

Synthesis of Oligonucleotide Analogues (1) Synthesis of Oligonucleotide (31)

The compound (30) was introduced into an oligonucleotide (0.2 μmol scale) by a DNA synthesizer (Expedite 8900). After treatment with ammonia, the product was purified by simplified reverse phase column chromatography (NENSORB™ PREP) and reverse phase HPLC (Wakopak®, 10 mm×25 cm, 8–16%, CH3CN in 35 min).

(2) Synthesis of Oligonucleotide (32)

Tetrakis(triphenylphosphine)palladium(0) (1.8 mg, 0.15 mmol) and sodium tetrahydroborate (2.1 mg, 6.9 mmols) were added to an H2O (297 μl) solution of the oligonucleotide (31) (98.0 nmols), and the mixture was stirred for 1 hour at room temperature. After filtration through a filter, the product was purified by reverse phase HPLC (Wakopak®, 10 mm×25 cm, 8–16%, CH3CN in 35 min) to obtain an intended deprotected compound (32) (31.5 nmols, 32%).

MALDI-TOF-Mass: calcd. 4492.00 [M–H]$^{-}$, found 4492.28 [M–H]$^{-}$.

EXPERIMENTAL EXAMPLE 1

Measurement (1–1) of Melting Temperature (Tm)

The melting temperature was measured in a 7 mM sodium phosphate buffer (pH 7.0) containing 140 mM of potassium chloride and 10 mM of magnesium chloride. The following oligonucleotide derivative (I) was synthesized, and its triplexes with target duplexes comprising the two DNA strands (II) and (III) were formed:

```
5'-d(TTTTTCTXTCTCTCT)-3'          (I)

5'-d(GCTAAAAAGAYAGAGAGATCG)-3'    (II)

3'-d(CGATTTTTCTZTCTCTCTAGC)-5'    (III)
```

Table 1 shows the melting temperature data on triplex-forming oligonucleotide dissociation.

TABLE 1

| 5'-d(TTTTTCTXTCTCTCT)-3' | | | | I |
| 5'-d(GCTAAAAAGAYAGAGAGYCG)-3' | | | | II |
| 3'-d(CGATTTTTCTZTCTCTCTAGC)-5' | | | | III |

| | Y · Z | | | |
|---|---|---|---|---|
| X | C · G | G · C | T · A | A · T |
| 4 | <u>33</u> | 19 | 14 | 23 |
| A | 21 | 21 | 18 | 24 |
| G | 20 | 23 | 27 | 16 |
| C | 25 | 43 | 16 | 18 |
| T | 25 | 20 | 17 | 44 |

C = 5-methylcytidine.
Conditions. 7 mM sodium phosphate buffer (pH 7.0), 140 mM KCl, 10 mM MgCl$_{2}$, [oligonucleotide] = 1.5 μM for each strand.

In the table, 4 denotes the compound 4 of the present invention, and C represents 5-methylcytidine. The oligonucleotide was 1.5 μM as each strand.

As clear from the results of Table 1, the oligonucleotide derivative containing the compound 4 of the present invention (X=4) formed triplexes with the target duplexes II•III (Y, Z) with very high sequence selectivity. The oligonucleotide derivative of the present invention showed the highest melting temperature (Tm=33° C.) for a CG base pair. This value was found to be better than that (Tm=25° C.) of the triplex (T•C•G) with thymine (T), a native nucleic acid base hitherto known to show the highest triplex-forming stability for a CG base pair.

The unexpected CG base pair-recognizing ability of the compound 4 of the present invention is assumed to be due to the sugar moiety having a fixed conformation and the presence of carbonyl oxygen at the 2-position in the pyridine base.

EXPERIMENTAL EXAMPLE 2

Measurement (1–2) of Melting Temperature (Tm)

The same test as in Experimental Example 1 above was conducted using the oligonucleotide derivatives having the following sequence, synthesized in Example 7, as triplex-forming oligonucleotides:

```
5'-d(TTTTTCTXTCTCTCT)-3'          (I)

5'-d(GCTAAAAAGAYAGAGAGATCG)-3'    (II)

3'-d(CGATTTTTCTZTCTCTCTAGC)-5'    (III)
```

Table 2 shows the melting temperature data on triplex-forming oligonucleotide dissociation.

TABLE 2

| | 5'-d(TTTTT$\underline{C}$TXT$\underline{C}$T$\underline{C}$T$\underline{C}$T)-3' | I |
|---|---|---|
| | 5'-d(GCTAAAAAGAYAGAGAGAYCG)-3' | II |
| | 3'-d(CGATTTTTCTZTCTCTCTAGC)-5' | III |

| | Y · Z | |
|---|---|---|
| X | T · A | dU · A |
| G | 27 | 24 |
| HB$^B$ | 27 | 41 |
| H$^B$ | 20 | 27 |

$\underline{C}$ = 5-methylcytidine. Conditions: 7 mM sodium phosphate buffer (pH 7.0), 140 mM KCl, 10 mM MgCl$_2$, [oligonucleotide] = 1.5 μM for each strand.

In the table, $\underline{C}$ represents 5-methylcytidine. HB$^B$ and H$^B$ denote, respectively, the sequences (I) in which, as X, a nucleotide analogue having 2-hydroxyphenyl instead of the nucleic acid base is used, and a nucleotide analogue having a hydroxyl group instead of the nucleic acid base is used. The oligonucleotide was 1.5 μM as each strand.

As clear from the results of Table 2, the oligonucleotide derivative containing the nucleotide analogue having 2-hydroxyphenyl according to the present invention (X=HB$^B$), when combined with the targeted duplex II•III (Y,Z=T•A), showed high stability, which was comparable to the stability of a G•T•A triplex and higher than the stability of an H$^B$•T•A triplex.

Then, when dU lacking in the 5-methyl group of T was used instead of T, a triplex (HB$^B$•dU•A) was formed which had the melting temperature (Tm) increased by 14° C. in comparison with the (T•dU•A) triplex.

The oligonucleotide derivatives containing the 2-hydroxyphenyl-containing nucleoside analogue of the present invention as a constituent element were confirmed to show an unexpected TA or dUA base pair recognizing ability.

EXPERIMENTAL EXAMPLE 3

Measurement (2) of Melting Temperature (Tm)

The nucleoside analogues of the present invention (5bc-PD, 5bc-MePD, 5bc-HPD, 5bc-liQL) were synthesized under the same conditions as in Experimental Example 1. Oligonucleotide derivatives containing these analogues were prepared, and their triplex-forming ability was investigated. At the same time, nucleoside analogues having various bases (including native nucleic acid bases) were similarly examined for the melting temperature.

The results are shown in Table 3. In connection with the tested nucleosides and nucleoside analogues, their structural formulas are shown. The sequence of the target double strand and the sequences of the triplex-forming oligonucleotides (TFO's) are also shown.

In the formulas, [$^m$C] denotes 5-methylcytidine.

TABLE 3

5'-TTTTT$^m$CTXT$^m$CT$^m$CT$^m$CT-3'
5'-GCTAAAAAGAYAGAGAGATCG-3'
3'-CGATTTTTCTZTCTCTCTAGC-5'

| | YZ | | | |
|---|---|---|---|---|
| X | CG | GC | TA | AT |
| A | 21 | 21 | 18 | 24 |
| G | 20 | 23 | 27 | 16 |
| 5bc-G | 19, 28 | 24 | 26 | 16, 22 |
| $^m$C | 25 | 43 | 16 | 18 |
| 5bc-$^m$C | 33 | 53 | 15 | 27 |
| T | 25 | 20 | 17 | 44 |
| 5bc-T | 35 | 31 | 16 | 57 |
| 5bc-oxa | 29 | 22 | 27 | 23 |
| 5bc-Im | 21 | 23 | 25 | 23 |
| 5bc-abasic | 24 | 20 | 20 | 16 |
| 5bc-PD | 33 | 19 | 14 | 23 |
| 5bc-MePD | 32 | 21 | 14 | 23 |
| 5bc-HPD | 32 | 28 | 15 | 27 |
| 5bc-liQL | 29 | 20 | 16 | 15 |

140 mM KCl, 10 mM MgCl$_2$, 7 mM Na$_2$HPO$_4$ buffer (pH 7.0)
each strand 1.5 μM
5° C. to 85° C. (0.5° C./min)
Target sequence:
5'-GCTAAAAAGAYAGAGAGATCG-3'
3'-CGATTTTTCTZTCTCTCTAGC-5'
TFO sequences:
5'-TTTTTCTXTCTCTCT-3'
5'-TTTTT$^m$CTXT$^m$CT$^m$CT$^m$CT-3'
Structures of 5bc-type nucleosides:

5bc-G

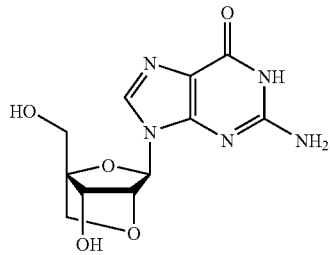

5bc-C

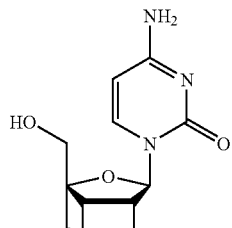

5bc-$^m$C

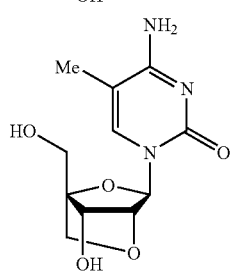

TABLE 3-continued

5′-TTTTT$^m$CTX T$^m$CT$^m$CT$^m$CT-3′
5′-GCTAAAAAGAYAGAGAGATCG-3′
3′-CGATTTTTCTZTCTCTCTAGC-5′

| X | YZ | | | |
|---|---|---|---|---|
|   | CG | GC | TA | AT |
| 5bc-T | | | | |
| 5bc-Phoxa | | | | |
| 5bc-oxa | | | | |
| 5bc-Im | | | | |
| 5bc-abasic | | | | |
| 5bc-PD | | | | |
| 5bc-MePD | | | | |
| 5bc-HPD | | | | |
| 5bc-1iQL | | | | |

As clear from the results of Table 3, the oligonucleotides of the present invention were able to specifically recognize the target DNA base pairs under pH conditions close to the in vivo conditions. The use of 5bc-PD as a nucleoside unit, in particular, gave Tm=33° C., showing high stability of the triplex, and showing the ability to specifically recognize a CG base pair with higher stability (10° C. or more) than for other base pair (AT base pair, Tm=23° C.).

INDUSTRIAL APPLICABILITY

The oligonucleotide derivatives of the present invention are useful as antigene triplex-forming oligonucleotide molecules which bind specifically to target double-stranded DNA with high affinity in the antigene method, and can thereby control the expression of particular genes efficiently. Particularly, the oligonucleotide derivatives specifically recognize a CG base pair present in a target sequence, which has so far been difficult to recognize, and bind to it with high affinity, forming a stable triplex. Thus, the oligonucleotide derivatives have enabled triplex formation targeted at duplex DNA of every sequence.

The oligonucleotide derivatives (TFO's) of the present invention are expected to be useful as pharmaceuticals for inhibiting the actions of particular genes and preventing and treating diseases. The oligonucleotide derivatives of the present invention may be labeled, for example, with fluorescence, and can thereby be used to detect double-stranded DNA having a particular nucleic acid sequence.

What is claimed is:

1. Nucleoside analogues expressed by the following general formula (I)

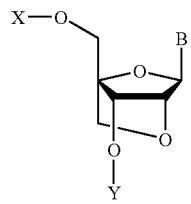

where B represents a substituent selected from substituents expressed by the following general formulas

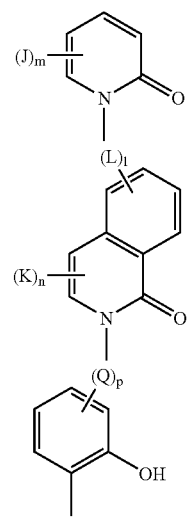

where J, K, L and Q are identical or different, and each denote —H, a lower alkyl, —OH, or —NH$_2$, l, m and p independently denote an integer of 1 to 4, and n denotes an integer of 1 or 2, X and Y are identical or different, and each represent hydrogen, an alkyl group, an alkenyl group, an alkinyl group, a cycloalkyl group, an aralkyl group, an aryl group, an acyl group, or a silyl group, or amidite derivatives thereof.

2. Nucleoside analogues or amidite derivatives thereof according to claim 1, wherein B represents a substituent expressed by any one of the following general formulas

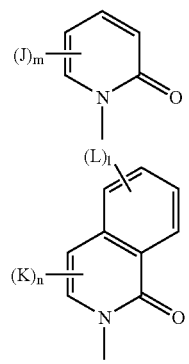

where J, K, L, l, m, X and Y are as defined above.

3. Nucleoside analogues or amidite derivatives thereof according to claim 1, wherein B represents a substituent expressed by the following general formula

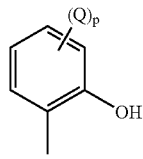

where Q, p, X and Y are as defined above.

4. Nucleoside analogues according to claim 1, 2 or 3, wherein X and Y are each hydrogen.

5. Amidite derivative according to claim 1, 2 or 3, wherein X is 4,4'-dimethoxytrityl (DMTr), and Y is a 2-cyanoethoxy (diisopropylamino)phosphino group (amidite group).

6. Nucleoside analogues according to claim 1 or 2, wherein B is a substituted or unsubstituted 2-oxopyridyl or a substituted or unsubstituted isoquinoline.

7. Nucleoside analogues according to claim 6, wherein B is selected from 2-oxopyridyl, 5-methyl-2-oxopyridyl, 4-hydroxy-2-oxopyridyl, and isoquinolin-1-one.

8. Nucleoside analogues according to claim 7, wherein B is 2-oxopyridyl.

9. Nucleoside analogues according to claim 1 or 3, wherein B is 2-hydroxyphenyl.

10. Oligonucleotide or polynucleotide derivatives having one or more of the nucleoside analogues according to any one of claims 1 to 3.

* * * * *

SEQUENCE LISTING

<160> NUMBER OF SEQ ID NOS: 4

<210> SEQ ID NO 1
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is a, c, g, or t

<400> SEQUENCE: 1 ttttctntc tctct                                                15

<210> SEQ ID NO 2
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is a, c, g, or t

<400> SEQUENCE: 2
gctaaaaaga nagagagatc g                                        21

<210> SEQ ID NO 3
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is a, c, g, or t

<400> SEQUENCE: 3
cgatttttct ntctctctag c                                        21

<210> SEQ ID NO 4
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)

```
<223> OTHER INFORMATION: n is a, c, g, or t

<400> SEQUENCE: 4
ttttnctnnc ncnct                    15
```